US009801751B2

(12) United States Patent
Wang

(10) Patent No.: US 9,801,751 B2
(45) Date of Patent: Oct. 31, 2017

(54) BACK PLATE OF WAIST SUPPORT

(71) Applicant: Meng-Chun Wang, Taichung (TW)

(72) Inventor: Meng-Chun Wang, Taichung (TW)

( * ) Notice: Subject to any disclaimer, the term of this patent is extended or adjusted under 35 U.S.C. 154(b) by 290 days.

(21) Appl. No.: 14/618,524

(22) Filed: Feb. 10, 2015

(65) Prior Publication Data

US 2016/0228278 A1 Aug. 11, 2016

(51) Int. Cl.
*A61F 5/02* (2006.01)
(52) U.S. Cl.
CPC .................................. *A61F 5/028* (2013.01)
(58) Field of Classification Search
CPC .......... A61F 5/028; A61F 5/024; A61F 5/026; A61F 13/14; A61F 5/03; A61F 5/449; A61F 5/24
USPC ........................................................ 602/19
See application file for complete search history.

(56) References Cited

U.S. PATENT DOCUMENTS 8,926,537 B2 * 1/2015 Ingimundarson ....... A61F 5/028 602/19
2014/0081189 A1 * 3/2014 Ingimundarson ....... A61F 5/028 602/19

* cited by examiner

*Primary Examiner* — Ophelia A Hawthorne
(74) *Attorney, Agent, or Firm* — Muncy, Geissler, Olds & Lowe, P.C.

(57) ABSTRACT

A back plate of a waist support includes a supporting section and two wings. The supporting section has a valley portion for receiving a wearer's spine. The two wings are symmetrically connected to the supporting section from two widthwise opposite sides thereof and each have plural lengthwise grooves, for making the wings of the back plate bendable. Thereby, the waist support is endurable and supportive and can effectively distribute the load that is focused on of the wearer's lumbar vertebrae.

11 Claims, 2 Drawing Sheets

BACK PLATE OF WAIST SUPPORT

BACKGROUND OF THE INVENTION

1. Technical Field

The present invention relates to waist supports, and more particularly to a back plate of a waist support.

2. Description of Related Art

For those having low-back pain, a waist support is an effective medial aid that eases the wearer's discomfort by distributing loads around his/her lumbar vertebrae. Thus, a patient having low-back pain is usually prescribed to wear a waist support in addition to performing rehabilitation and/or receiving treatment, with the expectation that his/her waist is supported and the effects of the rehabilitation/treatment can be enhanced.

A conventional waist support is mainly constructed from two elastic strips that are put around a wearer's waist and a back plate that is provided between the two elastic strips and supports the wearer's low back. However, such a back plate typically has a significant thickness and thus is not very bendable under the constricting force applied by the elastic strips. Consequently, the back plate usually fails to closely fit the wearer's body contours and has its supporting performance degraded. For making the back plate more conformable to the wearer's body contours, a common solution is to reduce its thickness, thereby increasing its bendability. Nevertheless, when the back plate becomes thinner, it also becomes less durable. For this reason, the known back plate needs to be improved.

SUMMARY OF THE INVENTION

The primary objective of the present invention is to provide a back plate of a waist support, which features for being endurable, supportive and capable of effectively distributing the load that is focused on of the wearer's lumbar vertebrae.

For achieving the foregoing objective, the disclosed back plate comprises a supporting section and two wings. The supporting section has a valley portion for receiving a wearer's spine. The two wings are connected symmetrically to two widthwise opposite sides of the supporting section and each has at least two lengthwise grooves for making the wings more bendable. Thereby, the disclosed back plate can be sufficiently bendable without reducing its thickness, so is endurable and supportive and can effectively distribute the load that is focused on of the wearer's lumbar vertebrae.

In one embodiment of the present invention, each said wing has a first lengthwise groove, a second lengthwise groove, and a third lengthwise groove. The first lengthwise groove extends curvedly in a direction in which the valley portion of the supporting section extends. The second lengthwise groove extends curvedly in the direction in which the valley portion of the supporting section extends and between the valley portion of the supporting section and the first lengthwise groove. The third lengthwise groove extends linearly in the direction in which the valley portion of the supporting section extends and between the first lengthwise groove and the second lengthwise groove.

DETAILED DESCRIPTION OF THE INVENTION

Figure 1:
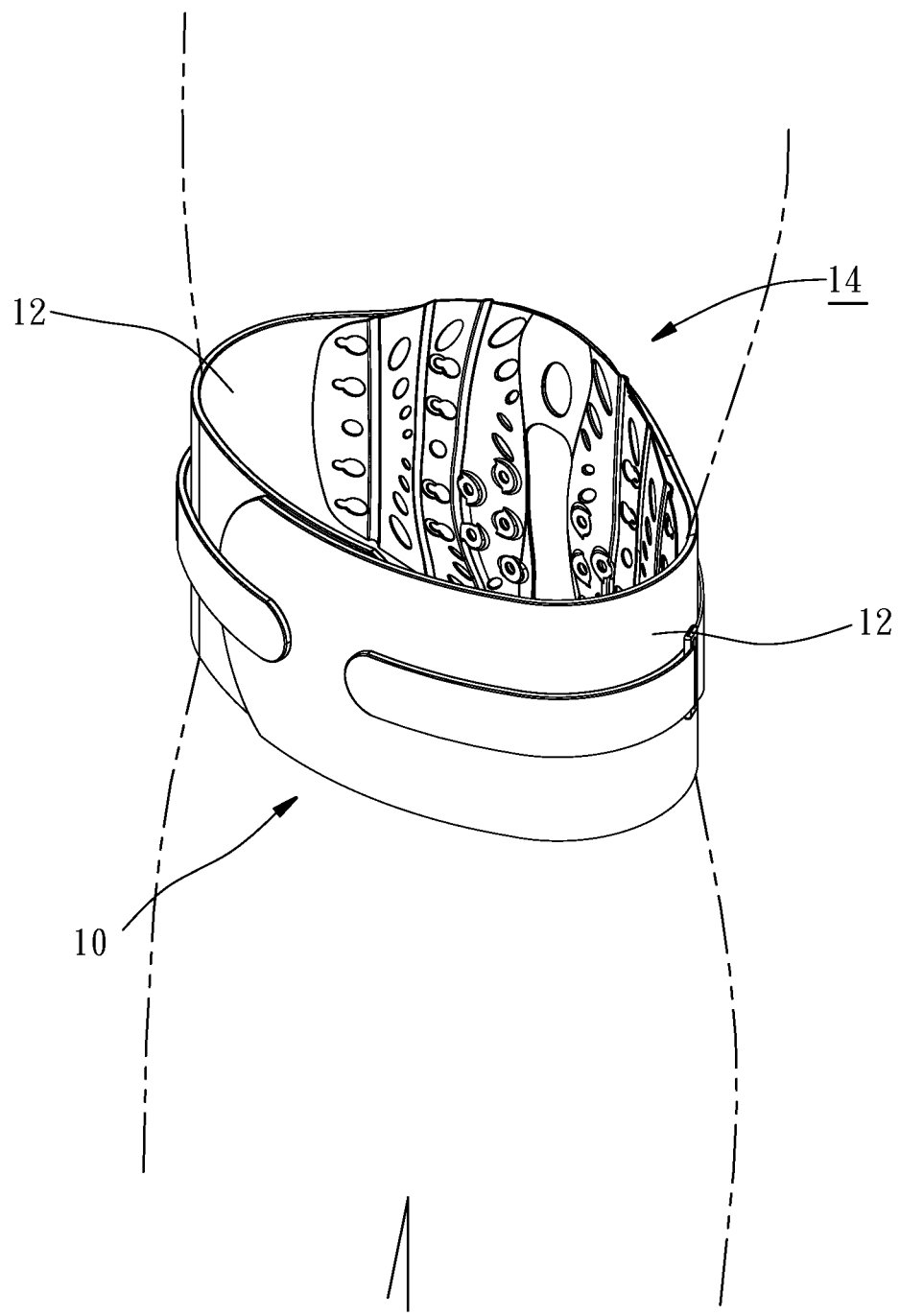
FIG. 1 is an applied view of the present invention working with elastic strips.
Figure 2:
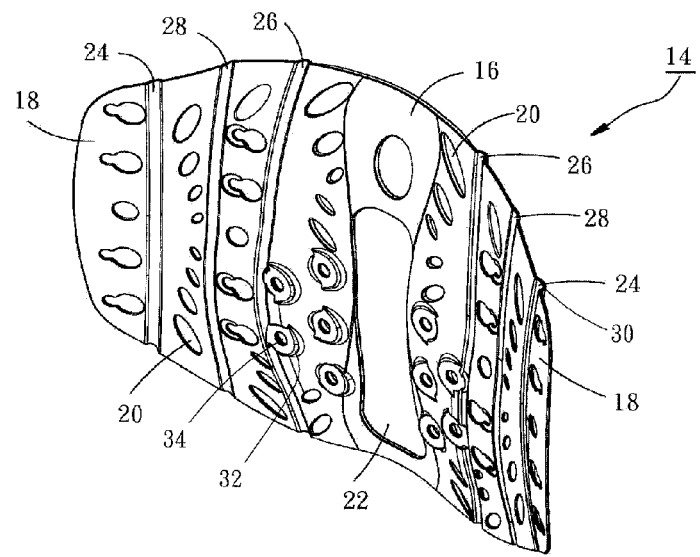
FIG. 2 is a perspective view of the present invention.

Referring to FIG. 2, according to the present invention, a back plate 14 comprises a supporting section 16 and two wings 18. Two elastic strips 12 are attached to the back plate 14 at the supporting section 16, so that the back plate 14 and the elastic strips 12 jointly form a waist support 10 (as shown in FIG. 1). The back plate 14 has a plurality of hollowed-out portions 20, for reducing the overall weight and allowing ventilation.

Figure 3:
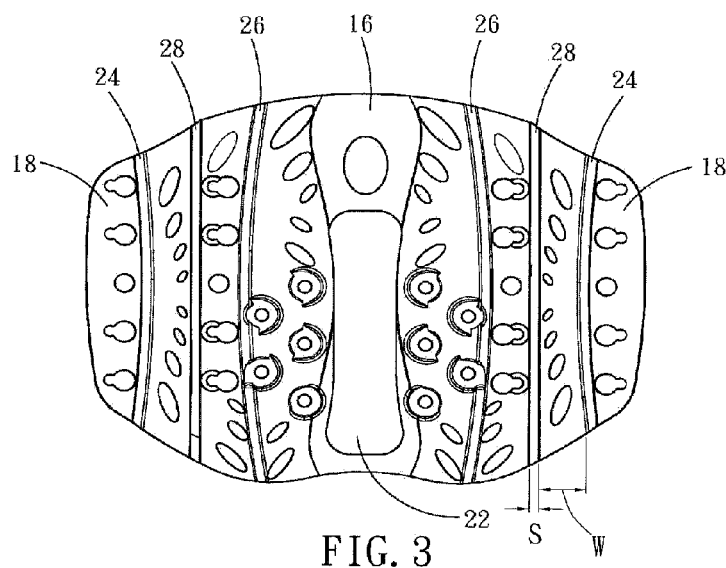
FIG. 3 is a front view of the present invention.

Referring to FIG. 3, the supporting section 16 of the back plate 14 is centrally provided with a valley portion 22, for receiving a wearer's spine. The wings 18 of the back plate 14 are connected symmetrically to two widthwise opposite sides of the supporting section 16 of the back plate 14. Each of the wings 18 of the back plate 14 has a first lengthwise groove 24, a second lengthwise groove 26, and a third lengthwise groove 28. The first lengthwise groove 24 extends curvedly in a direction in which the valley portion 22 extends. The second lengthwise groove 26 extends curvedly in the direction in which the valley portion 22 extends and between the valley portion 22 and the first lengthwise groove 24. The third lengthwise groove 28 extends linearly in the direction in which the valley portion 22 extends and between the first lengthwise groove 24 and the second lengthwise groove 26. In terms of arrangement, the first lengthwise groove 24 and the second lengthwise groove 26 are mirrored relative to each other about the third lengthwise groove 28. In terms of length, the second lengthwise groove 26 has a length greater than that of the third lengthwise groove 28, and the third lengthwise groove 28 has its length greater than that of the first lengthwise groove 24.

It is to be noted that the wings 18 of the back plate 14 in other embodiments may have two lengthwise grooves only, instead of three, as long as the lengthwise grooves are arranged symmetrically about the valley portion 22 of the supporting section. Each said lengthwise groove has a depth greater than a thickness of the wing and a radius of a curvature of each said lengthwise groove is smaller than that of the wing 18. Each said wing 18 further has at least two lengthwise ribs 30 corresponding to the at least two lengthwise grooves, and the at least two lengthwise ribs 30 and the at least two lengthwise grooves of a respective one of the two wings 18 are disposed on opposing sides of the back plate 14. Two adjacent grooves of the at least two lengthwise grooves have a widthwise interval W greater than a widthwise span S of any of the at least two lengthwise grooves of each said wing 18. Each said wing 18 has a plurality of projections 32 each having a through hole 34, and the plurality of projections 32 and all of the lengthwise grooves are disposed on the same side of the back plate 14. Part of the projections 32 extend within one of the lengthwise grooves. The first lengthwise groove 24 and the second lengthwise groove 26 are curved width-wise in opposite directions relative to the third lengthwise groove 28, the first lengthwise groove 24 is curved width-wise inwardly toward the valley portion 22, and the second lengthwise groove 26 is curved width-wise outwardly away from the valley portion 22.

In use of the waist support 10, the two elastic strips 12 are put on a wearer's waist first, and the back plate 14 is such positioned that the wearer's spine is received in the valley portion 22 of the supporting section 16. At last, the two elastic strips 12 are combined to hold the waist support 10 in position. When worn by the wearer, the waist support 10 has the wings 18 of the back plate 14 sufficiently bendable in virtue of the first, second and third lengthwise grooves 24, 26, 28 under the constricting force applied by the elastic strips 12, so that the back plate 14 as a whole can closely fit the wearer's body contours and properly support the wearer's lower back. Also, with the hollowed-out portions 20, ventilation is allowed, so the wearer can wear the waist support 10 for a longer period without feeling uncomfortable. As compared with the prior art, the disclosed back plate 14 can have a regular overall thickness while providing sufficient bendability, so as to make the waist support 10 endurable, supportive and capable of effectively distribute the load that is focused on of the wearer's lumbar vertebrae.

What is claimed is:

1. A back plate of a waist support, comprising: a supporting section and two wings, the supporting section having a valley portion, the two wings being connected symmetrically to two widthwise opposite sides of the supporting section and each said wing having at least two lengthwise grooves,
   wherein each said lengthwise groove has a depth greater than a thickness of the wing and a radius of curvature of each said lengthwise groove is smaller than that of the wing,
   wherein each said wing further has at least two lengthwise ribs corresponding to the at least two lengthwise grooves, and the at least two lengthwise ribs and the at least two lengthwise grooves of one of the two wings are disposed on opposing sides of the back plate, and
   wherein an adjacent two grooves of the at least two lengthwise grooves have a widthwise interval greater than a widthwise span of any of the at least two lengthwise grooves of each said wing.

2. The back plate of claim 1, wherein each said wing has a first lengthwise groove, a second lengthwise groove, and a third lengthwise groove, the first lengthwise groove extending curvedly in a direction in which the valley portion of the supporting section extends, the second lengthwise groove extending curvedly in the direction in which the valley portion of the supporting section extends and between the valley portion of the supporting section and the first lengthwise groove, and the third lengthwise groove extending linearly in the direction in which the valley portion of the supporting section extends and between the first lengthwise groove and the second lengthwise groove.

3. The back plate of claim 2, wherein the first lengthwise groove and the second lengthwise groove are mirrored relative to each other about the third lengthwise groove.

4. The back plate of claim 2, wherein the second lengthwise groove has a length greater than a length of the third lengthwise groove, and the length of the third lengthwise groove is greater than a length of the first lengthwise groove.

5. The back plate of claim 2, wherein the first lengthwise groove and the second lengthwise groove are curved widthwise in opposite directions relative to the third lengthwise groove, the first lengthwise groove is curved widthwise inwardly toward the valley portion, and the second lengthwise groove is curved widthwise outwardly away from the valley portion.

6. The back plate of claim 1, wherein the lengthwise grooves of the two wings are arranged symmetrically about the valley portion of the supporting section.

7. The back plate of claim 6, wherein each said wing has a first lengthwise groove, a second lengthwise groove, and a third lengthwise groove, the first lengthwise groove extending curvedly in a direction in which the valley portion of the supporting section extends, the second lengthwise groove extending curvedly in the direction in which the valley portion of the supporting section extends and between the valley portion of the supporting section and the first lengthwise groove, and the third lengthwise groove extending linearly in the direction in which the valley portion of the supporting section extends and between the first lengthwise groove and the second lengthwise groove.

8. The back plate of claim 7, wherein the first lengthwise groove and the second lengthwise groove are mirrored relative to each other about the third lengthwise groove.

9. The back plate of claim 7, wherein the second lengthwise groove has a length greater than a length of the third lengthwise groove, and the length of the third lengthwise groove is greater than a length of the first lengthwise groove.

10. The back plate of claim 1, wherein each said wing has a plurality of projections each having a through hole, and the plurality of projections and all of the lengthwise grooves are disposed on the same side of the back plate.

11. The back plate of claim 10, wherein part the projections extend within one of the lengthwise grooves.

* * * * *